United States Patent [19]

Van Scott et al.

[11] 3,984,566

[45] *Oct. 5, 1976

[54] METHOD OF ALLEVIATING THE SYMPTOMS OF DANDRUFF

[76] Inventors: Eugene J. Van Scott, 1138 Sewell Lane, Rydal, Pa. 19046; Ruey J. Yu, 4400 Dexter St., Philadelphia, Pa. 19128

[ * ] Notice: The portion of the term of this patent subsequent to Apr. 22, 1992, has been disclaimed.

[22] Filed: Mar. 7, 1975

[21] Appl. No.: 556,424

Related U.S. Application Data

[60] Division of Ser. No. 445,231, Feb. 25, 1974, Pat. No. 3,920,835, which is a continuation-in-part of Ser. No. 394,269, Sept. 4, 1973, Pat. No. 3,879,537.

[52] U.S. Cl............................ 424/283; 424/311; 424/317
[51] Int. Cl.² ........................................ A61K 31/35
[58] Field of Search.................... 424/311, 317, 283

[56] References Cited
UNITED STATES PATENTS

| | | | |
|---|---|---|---|
| 2,118,566 | 5/1938 | Miles | 424/317 |
| 3,124,506 | 3/1964 | Holman | 424/317 |
| 3,259,545 | 7/1966 | Teller | 424/68 |
| 3,608,086 | 9/1971 | Halpern | 424/317 |
| 3,666,863 | 5/1972 | Swanbeck | 424/317 |
| 3,879,537 | 4/1975 | Van Scott | 424/317 |

*Primary Examiner*—Norman A. Drezin
*Attorney, Agent, or Firm*—LeBlanc & Shur

[57] ABSTRACT

A treatment to alleviate the symptoms of diseases characterized by defects in keratinization consisting of the topical application of an ointment or lotion containing one or more lower aliphatic compounds having from 2 to about 6 carbon atoms, and preferably having α-carbon functionality is disclosed. The compounds include α-hydroxy acids, keto acids and esters thereof, and 3-hydroxybutyric acid. The therapeutic composition may include one or more of the commmpounds present in a total amount of from one to twenty percent in either a water or alcohol solution or an ointment. Topical application to affected areas has been found to achieve a complete remission of dandruff, acne and palmar and plantar hyperkeratosis.

5 Claims, No Drawings

METHOD OF ALLEVIATING THE SYMPTOMS OF DANDRUFF

This application is a division of Ser. No. 445,231 filed Feb. 25, 1974, now U.S. Pat. No. 3,920,835, which in turn is a continuation-in-part of application Ser. No. 394,269 filed Sept. 4, 1973, now U.S. Pat. No. 3,879,537.

This invention relates to a treatment for diseases characterized by defective keratinization including dandruff, acne and palmar and plantar hyperkeratosis, and specifically to compounds which have been found to be effective when topically applied, to heal the skin lesions associated with these diseases in humans.

Disease conditions characterized by defects in keratinization are relatively common and many different treatments have been prescribed in the past with varying degrees of effectiveness. In each of these disease conditions the process whereby the epidermal cells mature and form a surface layer (stratum corneum) is defective. Therefore, the signs and symptoms of diseases associated with defective keratinization are an overproduction of cells and/or their retention in the stratum corneum for abnormally prolonged periods.

In our parent application Ser. No. 394,269 filed Sept. 9, 1973 end entitled TREATMENT OF ICHTHYOSIFORM DERMATOSES a treatment was described for ichthyosis, a fish-scale-like appearance of the human skin. Ichthyosiform dermatoses are hereditary disorders characterized by excessive amounts of scale which accumulate on the skin surface.

As described in our aforementioned parent application, certain lower aliphatic compounds having 2 to about 6 carbon atoms and preferably having α-carbon functionality were found to be effective against ichthyotic conditions in humans, and to cause a remission thereof and healing of the lesions. Lotions or ointments formulated with one or more α-hydroxy acids, keto acids and esters thereof, or 3-hydroxybutyric acid present in from one to about twenty percent by weight were found to achieve complete remission of ichthyosis in humans.

Prior to this invention conventional treatments for ichthyotic conditions involved the topical application of hydrating emollients. In addition, ointments containing salicylic acid or vitamin A acid were also used, and in many cases these treatments were found to be unable to promote healing.

It has now been discovered that the above treatment has wider application against many disease conditions characterized by defective keratinization, such as dandruff, acne, and callous-forming disorders such as palmar and plantar hyperkeratosis. These conditions are also alleviated by treatment with one or more α-hydroxy acids, keto acids and esters thereof or 3-hydroxybutyric acid. It has also been discovered that the lotions or ointments formulated according to the teachings of our parent application Ser. No. 394,269, filed Sept. 4, 1973 are effective to cause a complete remission of the symptoms of the aforementioned keratinization disorders. Accordingly, the disclosure of our aforedescribed parent application is hereby incorporated by reference.

At least one of the several compounds to be hereinafter described also have been found to be effective against the above diseases when applied topically to the affected areas. The compounds are generally characterized as organic acids and esters thereof, having from 2 to 6 carbon atoms and having α and in some case β-carbon functionality. The compounds include α-hydroxy substituted acids, keto acids having α-carbon functionality, their esters, and 3-hydroxybutyric acid. The compounds tested and found to be effective are glycolic acid, citric acid, lactic acid, malic acid, tartronic acid, tartaric acid, glucuronic acid; the keto acid, pyruvic acid, together with its ethyl and methyl esters; 2-hydroxyisobutyric acid and 3-hydroxy butyric acid.

It should be emphasized, however, that although other compounds within the aforementioned designation may be found to be effective, many are not. For example, fumaric and succinic acids were found to be totally ineffective in causing remissions of ichthyosis.

It has been established through extensive tests on animals and humans that in addition to being effective in humans to cause a remission of ichthyotic conditions, topical application of solutions or ointments containing from 1 to 20% of at least one of the above compounds, and preferably from 5 to 10% thereof is effective against diseases relating to keratinization such as dandruff, acne, and palmar and plantar hyperkeratosis. It has also been discovered that when applied on a daily basis within about one to two weeks the affected areas will return to a normal skin condition. Furthermore, two or more compounds may be used in a composition of this invention. However, the total concentration of the compounds is preferred not to exceed about 10% by weight of the composition.

Accordingly, it is an object of this invention to provide a medicinal composition containing at least one lower organic hydroxy acid, keto acid, and esters thereof, which when topically applied will reliably alleviate the symptoms of skin conditions characterized by defects in keratinization.

It is another object to provide a medicinal composition for the treatment of skin disorders relating to the overproduction of cells and/or their retention in stratum corneum, which diseases include dandruff, acne and palmar and plantar hyperkeratosis.

It is another object to provide a method for treating diseases characterized by defective keratinization with a nontoxic ointment or solution of water or alcohol soluble lower organic compounds.

It is another object to provide a safe and efficient method for treating the symptoms of dandruff, acne, or callous forming disorders through regular topical application of a medicinal composition which will promote healing within about 1 to 2 weeks.

It is still another object to provide a method for treating diseases characterized by defective keratinization by topical application of a composition containing at least one organic acid or ester thereof having from 2 to 6 carbon atoms and having α-carbon functionality which is effective to promote healing of the affected areas.

It is still another object of this invention to provide a method for formulating a medicinal composition in ointment or lotion form which when applied at least daily, topically, to lesions, characterized by defective keratinization, will result in restoration of a normal, healthy skin condition.

It is yet another object of this invention to provide a medicinal composition useful for topical application to treat dandruff, acne, and palmar and plantar hyperkeratosis including a water or alcohol solution of lower aliphatic acids, keto acids and their esters, having from 2 to 6 carbon atoms and α-carbon functionality wherein at least one of said acids is present in said composition in from 1 to 20% by weight.

Specifically, the compounds of this invention found to be useful in the treatment of diseases characterized by overproduction of cells and/or their retention in the stratum corneum for abnormally long periods are the α-hydroxy acids having from two to six carbon atoms, glycolic acid, lactic acid, citric acid, malic acid, tartronic acid, tartaric acid, and glucoronic acid; the keto acid, pyruvic acid, and its methyl and ethyl esters; 2-hydroxyisobutyric acid and 3-hydroxybutyric acid.

Certain of the above compounds are well known additives in cosmetic compositions. See *The New Cosmetic Formula* H. Bennet, Chemical Publishing Company, Inc., New York (1970). For example, citric acid is a well known additive for shampoo formulations. Citric acid, however, is used therein in small quantities of less than 1% to adjust the acidity of the composition. It has been discovered, however, that therapeutically effective concentrations of from 1 to 20% and preferably from 5 to 10% of the above compounds will exert a normalizing effect on a hyperkeratinization condition.

Although it was initially discovered that the compounds of this invention were individually or collectively effective against the hereditary disease ichthyosis, further investigation has determined that these compounds are therapeutically effective against a wide ranging group of disorders characterized by hyperkeratinization wherein there is an overproduction of cells or the cells are retained in the stratum corneum for abnormally prolonged periods. Accordingly, although it is well known to add less than 1% thereof to cosmetic lotions, shampoos, and the like to adjust the acidity of the composition, it is not known prior to this invention to use from a 1% up to a 20% concentration of these compounds to formulate a therapeutically beneficial lotion or ointment effective against dandruff, acne, or palmar or plantar hyperkeratosis.

Preparation of the Therapeutic Compositions

In the above referenced parent patent application the preparation of the therapeutically effective compositions containing the above compounds was described. The same procedure is also applicable to formulate the compositions of this invention.

To summarize, however, at least one compound of this invention is preferably dissolved in water or ethanol initially. A solution thus prepared may be admixed in a conventional manner with any commonly available ointment base such as hydrophilic ointment (USP) or petrolatum (USP).

The concentration ranges are as noted above from 1 to 20% by weight of the total composition. The preferred concentration range, however, is from 5 to 10%.

If desired two or more of the compounds of this invention may be dissolved and admixed in an ointment as described above to form the composition of this invention. In this instance, it is preferred that the concentration of the compounds not exceed a total of about 10% by weight.

The water or ethanol used to dissolve the compounds according to this invention may range in concentration of from 1 to 30%, by volume, of the total composition. The preferred concentration thereof, however, is 10% by volume.

It has been found that the therapeutic ointments of this invention, prepared as above, may be stored in ointment jars at room temperature for extended periods of time without change in clinical effectiveness.

The above compounds may also be prepared in a solution or lotion form. A typical solution of this invention utilizes at least one of the compounds of this invention, dissolved directly in a mixture of water, ethanol and propylene glycol in a preferred weight ratio of 40:40:20, respectively. The ratio of each vehicle may vary; however, the preferred concentration of ethanol and propylene glycol should not exceed 70% and 30%, respectively. When solutions are formulated according to this invention, the compound concentration range may be from 1 to 20% by weight, as noted above. In addition, a concentration of from 5 to 10% is preferred. One or more of the compounds may also be admixed to a total concentration not exceeding about 10% by weight, as also described above.

The following are illustrative examples of formulations of compositions according to this invention. Although the examples utilize only selected members of the above listed compounds, useful according to this invention, it should be understood that the following examples are illustrative and not limited. Therefore, any of the above compounds may be substituted according to the teachings of this invention in the following formulations.

EXAMPLE 1

A glycolic acid 5% solution is prepared as follows: Glycolic acid, 5 grams, was dissolved in 5 mls of water and the solution admixed with 40 mls of ethanol and 20 mls of propylene glycol. Sufficient water was added to make 100 mls of composition.

EXAMPLE 2

An ethyl pyruvate 1% solution was prepared as follows: 1 ml ethyl pyruvate was admixed with 5 mls water and added to 50 mls ethanol and 20 mls propylene glycol. Sufficient water was then added to make 100 mls of the composition of this invention.

EXAMPLE 3

A solution of combined compounds was prepared as follows: 1 gram glycolic acid, 1 ml pyruvic acid, 1 ml lactic acid, 1 gram tartronic acid, and 1 gram citric acid were dissolved in about 10 mls of water and the solution admixed with 40 mls ethanol and 20 mls propylene glycol. Sufficient water was then added to make 100 mls of solution.

EXAMPLE 4

An ethyl pyruvate 5% ointment was prepared as follows: 5 mls ethyl pyruvate was admixed with 95 grams USP grade hydrophilic ointment, directly, until a uniform consistency resulted.

Additional procedures for formulating ointments according to this invention are described in the aforementioned parent patent application the disclosure of which is herein incorporated by reference.

Test Results

Each of the above mentioned compounds was initially subjected to a series of screening tests with mice. These tests are described in the above noted parent application and the disclosure thereof is hereby incorporated by reference.

Dandruff

Following the screening tests, and tests successfully treating ichthyosis, a glycolic acid 5% solution was prepared as described above with relation to Example 1. Five patients with severe dandruff problems were instructed to rub into the scalp the above 5% solution twice weekly. This topically applied solution prevented all signs of dandruff, i.e., formation of scales on the scalp in all five patients. Relief was observed within about a week in each case and normal skin condition was observed to be maintained at least one to two weeks after treatment was terminated.

Acne

A 1% ethyl pyruvate solution was prepared according to the procedures set forth in Example 2 above. Seven patients with acne were instructed to apply the above preparation topically twice daily on the skin of the face for 4 weeks. Six of the seven patients tested showed substantial reduction in the number of acne lesions after 4 weeks of topical treatment.

A combined solution was prepared according to the procedure described above with relation to Example 3. Seven patients with moderate to severe acne were instructed to apply the above preparation, topically, twice daily on the affected areas. All patients showed a substantial reduction in the number of acne lesions after 4 weeks of treatment.

Callouses

An ethyl pyruvate 5% ointment was prepared according to the procedure outlined above with relation to Example 4. Six patients with palmar and plantar callouses secondary to chronic eczema or chronic friction were instructed to apply the above preparation topically, twice daily, to affected areas. All patients showed a substantial improvement after 2 weeks of treatment.

In summary, it has now been discovered that certain aliphatic compounds are effective against disorders characterized by hyperkeratinization. While in our parent application these compounds were described and claimed as therapeutically effective in ointment or solution against ichthyosis, it has now been discovered that these compounds are capable of a generic application to diseases characterized by hyperkeratinization, such as dandruff, acne, and callous forming disorders. The compounds are formulated as described above and have been found in nearly all cases to achieve a complete restoration of normal appearing skin. The method of application utilized herein generally requires daily applications, and the lesions ordinarily were substantially cleared after about 1 week of treatment.

Treatment with the compositions of this invention, however, has not been found to result in a permanent cure. When regular application of the composition of this invention is terminated, normal appearing skin will remain for varying periods of time from several days to several months depending upon the patient. However, when regular application is resumed the lesions again disappear and normal appearing skin is restored.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A method of alleviating the symptoms of dandruff comprising topically applying an effective amount of a medicinal composition to the involved portions of the human body, said composition comprising from about 1% to about 20% by weight of a compound selected from the group consisting of glycolic acid, citric acid, malic acid, tartronic acid, tartaric acid, glucuronic acid, pyruvic acid, ethyl pyruvate, methyl pyruvate, 2-hydroxyisobutyric acid and 3-hydroxy butyric acid in admixture with a pharmaceutically acceptable carrier.

2. The method of claim 1 wherein said compound is present in from 5% to about 10% by weight.

3. The method of claim 1 wherein said composition is an ointment containing said compound dissolved in about 1% to about 30% by volume of a solvent selected from the group consisting of water and ethanol, and admixed with an ointment base selected from the group consisting of petrolatum and hydrophilic ointment.

4. The method of claim 1 wherein said compound is dissolved in a mixture of water and ethanol and propylene glycol, said ethanol being present in no more than about 70% by weight and said propylene glycol present in no more than about 30% by weight.

5. The method of claim 4 wherein the liquid is an admixture of water, ethanol, and propylene glycol present in a ratio of 40:40:20.

\* \* \* \* \*